US009706969B2

(12) United States Patent
Takei

(10) Patent No.: US 9,706,969 B2
(45) Date of Patent: Jul. 18, 2017

(54) MEDICAL IMAGE DIAGNOSIS APPARATUS

(71) Applicant: Toshiba Medical Systems Corporation, Otawara-shi (JP)

(72) Inventor: Koji Takei, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 7 days.

(21) Appl. No.: 14/711,151

(22) Filed: May 13, 2015

(65) Prior Publication Data

US 2015/0327820 A1 Nov. 19, 2015

(30) Foreign Application Priority Data

May 14, 2014 (JP) ................................ 2014-100823

(51) Int. Cl.
| A61B 6/00 | (2006.01) |
| A61B 6/04 | (2006.01) |
| A61B 6/03 | (2006.01) |
| A61B 6/02 | (2006.01) |

(52) U.S. Cl.
CPC .............. A61B 6/488 (2013.01); A61B 6/027 (2013.01); A61B 6/035 (2013.01); A61B 6/0407 (2013.01); A61B 6/0457 (2013.01); A61B 6/4482 (2013.01); A61B 6/461 (2013.01); A61B 6/465 (2013.01); A61B 6/547 (2013.01); *A61B 6/032* (2013.01)

(58) Field of Classification Search
CPC ........... A61B 6/582; A61B 6/08; A61B 6/461; A61B 6/589; A61B 6/508; A61B 6/4441; G06T 5/50; G06T 7/0081; G06T 7/0038; G06T 19/006; G06T 2207/10016; G06T 2219/2004; G06T 2210/41; G09G 3/2003
USPC .................................................... 378/20, 206
See application file for complete search history.

(56) References Cited

U.S. PATENT DOCUMENTS

| 2008/0187097 A1* | 8/2008 | Cheng .................... A61N 5/107 378/65 |
| 2011/0249793 A1* | 10/2011 | Lalena ..................... A61B 6/46 378/62 |
| 2013/0077745 A1* | 3/2013 | Wang ....................... A61B 6/52 378/62 |
| 2013/0198200 A1* | 8/2013 | Takei ................ G06F 17/30619 707/741 |
| 2014/0328456 A1* | 11/2014 | Lee ...................... A61B 6/4452 378/28 |

FOREIGN PATENT DOCUMENTS

JP 2008-119449 5/2008

* cited by examiner

*Primary Examiner* — Michael Maskell
(74) *Attorney, Agent, or Firm* — Oblon, McClelland, Maier & Neustadt, L.L.P.

(57) ABSTRACT

According to one embodiment, a medical image diagnosis apparatus is capable of imaging a subject based on a scan plan. The medical image diagnosis apparatus includes a gantry, a bed, a display, and a controller. The gantry images the subject. The bed includes a top-plate upon which the subject is positioned. The display is attached to the gantry. The controller displays, based on the scan plan, one of a moving distance of the top-plate, a moving direction of the top-plate, and a scan mode based on the scan plan.

9 Claims, 10 Drawing Sheets

| Scan mode | Scan name |
|---|---|
| S&V | Scan&View |
| S&S | Scan&Scan |
| Helical | Helical |
| vHP | Variable Helical Pitch |
| GG-Hel | Go&Go Helical |
| GR-Hel | Go&Return Helical |
| Sh-Helical | Shuttle Helical |

MEDICAL IMAGE DIAGNOSIS APPARATUS

CROSS-REFERENCE TO RELATED APPLICATIONS

This application is based upon and claims the benefit of priority from the Japanese Patent Application No. 2014-100823, filed May 14, 2014, the entire contents of which are incorporated herein by reference.

FIELD

Embodiments described herein relate generally to a medical image diagnosis apparatus.

BACKGROUND

An X-ray Computed Tomography apparatus (X-ray CT apparatus), a Positron Emission Tomography-CT apparatus (PET-CT apparatus) and a Magnetic Resonance Imaging apparatus (MRI apparatus) have been used in clinical sites. Recently, a multi-row system X-ray CT apparatus has become mainstream. This type of X-ray CT apparatus can perform not only a conventional normal scan, but also a helical scan for spirally scanning a subject, and dynamic time phase imaging.

In accordance with technical progress in modality, many scan modes (scan types), such as scanogram imaging, a helical scan, and a dynamic scan, have become available. In addition to imaging in a single mode, imaging based on an imaging plan (scan plan) made by a time-series combination of multiple modes has become typical.

A top-plate of a bed freely moves to move a subject in accordance with the scan plan. In such imaging, a problem arises when a medical appliance (such as a medical tube) is connected to a subject. In some cases, a subject connected to a tube from an injector for injection of a contrast agent or an infusion tube needs to be imaged. A blood flowmeter, a sphygmomanometer, or a sphygmometer is also often connected to a subject. However, when, for example, the top-plate moves in a direction which an infusion tube that is stretched to some extent is further extended, the tube may be pulled too far and come out. For example, a blood transfusion tube getting pulled out of a patient can endanger their life.

When existing apparatuses are used, medical appliances need to be very carefully arranged in an examination room since it is difficult to tell how far and in which direction the top-plate moves. A technician in an examination room cannot easily tell whether the top-plate gradually moves as in helical imaging, or moves for every scan as in multi-row imaging. A technician communicates with an operator in a console room, and places appliances while paying attention to safety. However, the scan plan varies by patient, and a technician needs to expend considerable time and effort in finding an arrangement that satisfies conditions of the examination room. Elimination of such inconvenience has been desired by medical service workers such as technicians, nurses, and operators, as well as patients.

DETAILED DESCRIPTION

In general, according to one embodiment, a medical image diagnosis apparatus is capable of imaging a subject based on a scan plan. The medical image diagnosis apparatus includes a gantry, a bed, a display, and a controller. The gantry images the subject. The bed includes a top-plate upon which the subject is positioned. The display is attached to the gantry. The controller displays, based on the scan plan, one of a moving distance of the top-plate, a moving direction of the top-plate, and a scan mode based on the scan plan.

Figure 1:
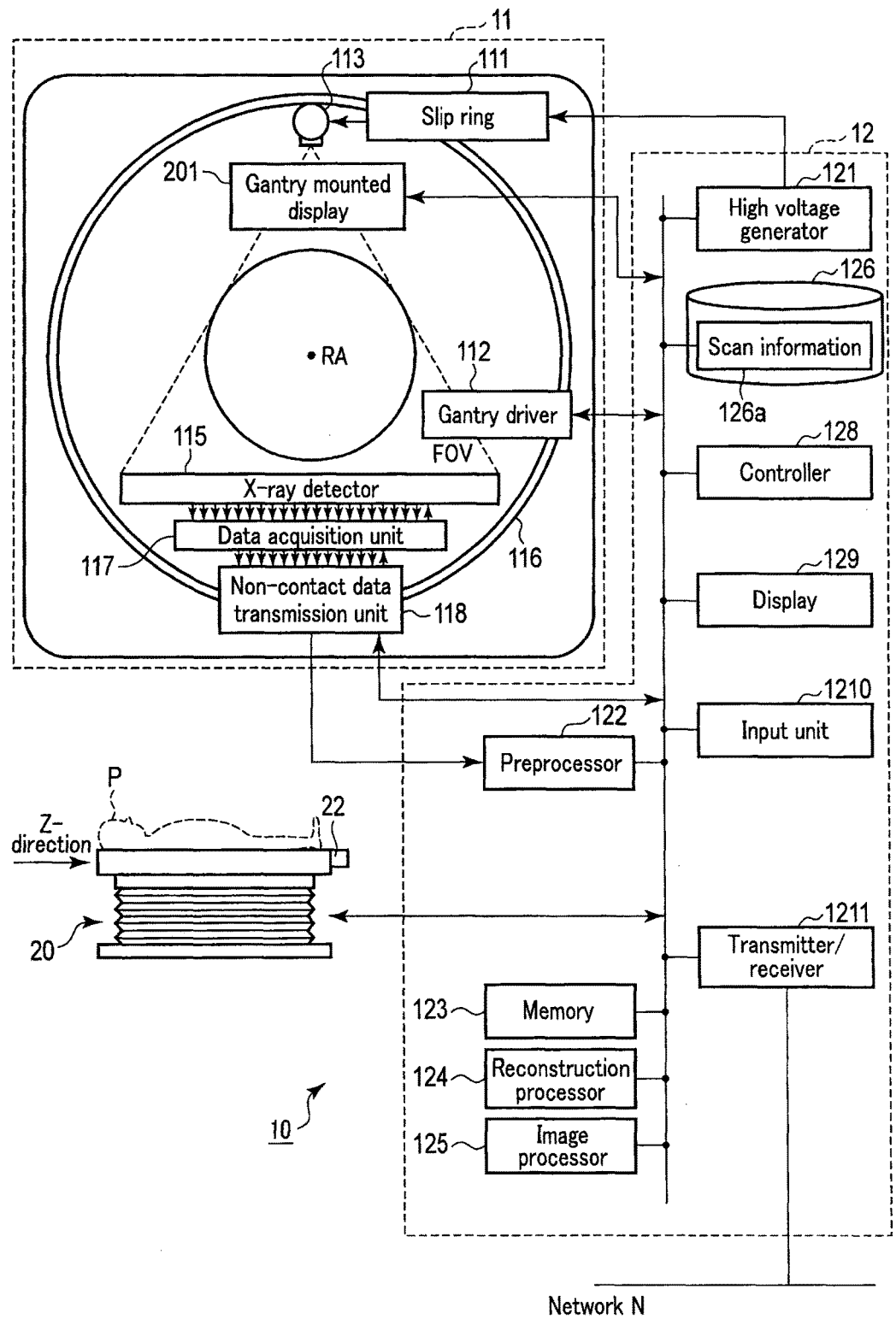
FIG. 1 is a block diagram showing an example of a medical image diagnosis system 10 according to the first and second embodiments.

FIG. 1 is a block diagram showing an example of a medical image diagnosis system 10 according to the first and second embodiments. The medical image diagnosis apparatus is, for example, an X-ray CT apparatus, a PET apparatus, a PET-CT apparatus, or an MRI apparatus. Herein, the X-ray CT apparatus is used as an example for explanation. In particular, assumed herein is an X-ray CT apparatus capable of setting a scan plan, and imaging a subject based on the scan plan.

The medical image diagnosis system 10 shown in FIG. 1 includes a gantry 11, a bed 20, and an information processor 12. The gantry 11 and the bed 20 are placed in an examination room, and the information processor 12 is placed in a separate console room.

The gantry 11 radiates X-rays to a subject P to image the subject P. Projection data on the subject P is thereby acquired. The gantry 11 includes a slip ring 111, a gantry driver 112, an X-ray tube 113, an X-ray detector 115, a rotating frame 116, a data acquisition unit 117, a non-contact data transmission unit 118, and a gantry mounted display 201.

The bed 20 includes a top-plate 22 upon which the subject P is positioned. The top-plate 22 moves mainly in the Z-direction based on a control signal supplied by the information processor 12. For fine adjustment, the top-plate 22 may move in an X-direction or Y-direction perpendicular to the Z-direction. By moving the top-plate 22, the subject P can be moved into or moved out of an imaging field of view of the gantry 11.

The information processor 12 controls data acquisition processing at the gantry 11. The information processor 12 also performs known processing on data acquired by the gantry 11, and generates an X-ray image and various clinical information. The information processor 12 includes a high voltage generator 121, a preprocessor 122, a memory 123, a reconstruction processor 124, an image processor 125, a storage unit 126, a controller 128, a display 129, an input unit 1210, and a transmitter/receiver 1211.

The gantry driver 112 rotates the rotating frame 116. This rotation makes the X-ray tube 113 and the X-ray detector 115 rotate about a body axis of the subject P in such a manner that the X-ray tube 113 faces the X-ray detector 115.

The X-ray tube 113 is a vacuum tube for generating X-rays, and is provided on the rotating frame 116. The high voltage generator 121 supplies power (tube current and tube voltage) necessary for radiation of X-rays to the X-ray tube 113 via the slip ring 111. The X-ray tube 113 generates X-rays by accelerating electrons of the supplied high voltage and having the electrons collide with a target. The subject P mounted in a Field of View (FOV) is radiated with the X-rays.

The X-ray detector 115 detects X-rays which has passed through the subject P. The X-ray detector 115 is a single-slice-type or multi-slice-type detector system. The X-ray detector 115 is attached to the rotating frame 116 to face the X-ray detector 113. The X-ray detector 115 includes a plurality of detector elements, each of which is made of a combination of a scintillator and a diode. The detector elements are one-dimensionally or two-dimensionally arranged in accordance with the type of the X-ray detector 115.

The rotating frame 116 is a ring which rotates about the Z-axis, and is provided with the X-ray tube 113 and the X-ray detector 115. The center part of the rotating frame 116 is open. The subject P mounted on the top-plate 22 is inserted in the opening.

The data acquisition unit 117, which is a Data Acquisition System (DAS), converts a signal output for each channel from the detector 15 into a voltage signal, amplifies the voltage signal, and converts the voltage signal into a digital signal. The data (raw data) is taken in the information processor 12 via the non-contact data transmission unit 118.

The high voltage generator 121 includes, for example, a high voltage converter, a filament heating converter, a rectifier, and a high voltage switch (not shown). The high voltage generator 121 supplies power necessary for radiation of X-rays to the X-ray tube 113 via the slip ring 111.

The preprocessor 122 receives raw data from the data acquisition unit 117 via the non-contact data transmission unit 118, and makes a sensitivity correction and an X-ray intensity correction. The 360-degree corrected raw data is temporarily stored in the storage unit 126. The raw data subjected to preprocessing by the preprocessor 122 is called "projection data."

The storage unit 126 stores scan information 126a relating to a subject, in addition to medical image data such as raw data and projection data. The scan information 126a is, for example, a scan plan determined in a past CT scan of a subject, or a scan plan determined based on a scanogram. The scan information 126a may include information on an installation position of a contrast agent injector placed in an examination room, a length of an injection tube, and a length of an infusion tube, for example.

The reconstruction processor 124 reconstructs image data by a reconstruction method selected by a user. A plurality of reconstruction methods, such as a fan beam reconstruction method (which is also called "fan beam convolution back-projection method"), a Feldkamp method, and a cone beam reconstruction method, are known.

The image processor 125 performs image processing for display (such as window conversion or RGB processing) on reconstructed image data generated by the reconstruction processor 124, and outputs processed data to the display 129. The image processor 125 generates a quasi-three-dimensional image based on instructions of an operator, and outputs the quasi-three-dimensional image to the display 129. The quasi-three-dimensional image may include a tomography image of any cross-section, a projection image in any direction, and a three-dimensional surface image, for example.

The display 129 is an output device which displays a computer tomography image or a CT image such as a scanogram image. CT values of the CT image are a relative value of an X-ray absorption coefficient of a substance with respect to that of a reference substance (such as water).

The input unit 1210 is a user interface including a keyboard, various switches, and a mouse, for example. An operator (including a technician) inputs various scan conditions such as a slice thickness and a slice number to the system by means of the input unit 1210.

The transmitter/receiver 1211 communicates with other medical devices through a network N, and transmits/receives image data and patient information, for example. Digital Imaging and Communications in Medicine (DICOM) is a typical communication protocol. In particular, the transmitter/receiver 1211 receives information on imaging of a subject from a server device (not shown) connected to the network N. The transmitter/receiver 1211 transmits an acquired medical image to an image server (not shown) connected to the network N.

Each function of the preprocessor 122, the reconstruction processor 124 and the image processor 125 may, for example, be stored in the memory 126 in a form of program that is executable by the controller 128.

By reading out the program from a memory circuitry (memory 126) and executing it, the controller 128 comprises a processor which realizes a function corresponding to each program. In other words, a processing circuitry in a state where each program has been read out will comprise each function shown in the information processor (computer) 12 of FIG. 1.

Instead of storing the program in the memory circuitry, it is also possible to integrate the program directly into the processing circuitry. In this type of form, the processor realizes the functions by reading out and executing the programs integrated in the circuitry.

FIG. 1 exemplifies the matter of the single computer realizing the functions of the preprocessor 122, the reconstruction processor 124 and the image processor 125 by a single processor (controller 128). Instead, it is also fine to configure a processing circuitry by combining a plurality of independent processors, and realize each function by having each processor execute the program.

The term "processor" used in the above explanation indicates, for example, a circuit of a CPU (central processing unit), a GPU (Graphics Processing Unit), or an Application Specific Integrated Circuit (ASIC), Programmable Logic Devices (for example, a Simple Programmable Logic Device (SPLD), a Complex Programmable Logic Device (CPLD), and a Field Programmable Gate Array (FPGA)).

The medical image diagnosis system 10 shown in FIG. 1 includes the gantry mounted display 201. The gantry mounted display 201 is, for example, a liquid crystal monitor, and is attached to the gantry 11 at an easily-viewable position, such as an upper part of the front panel.

Figure 2:
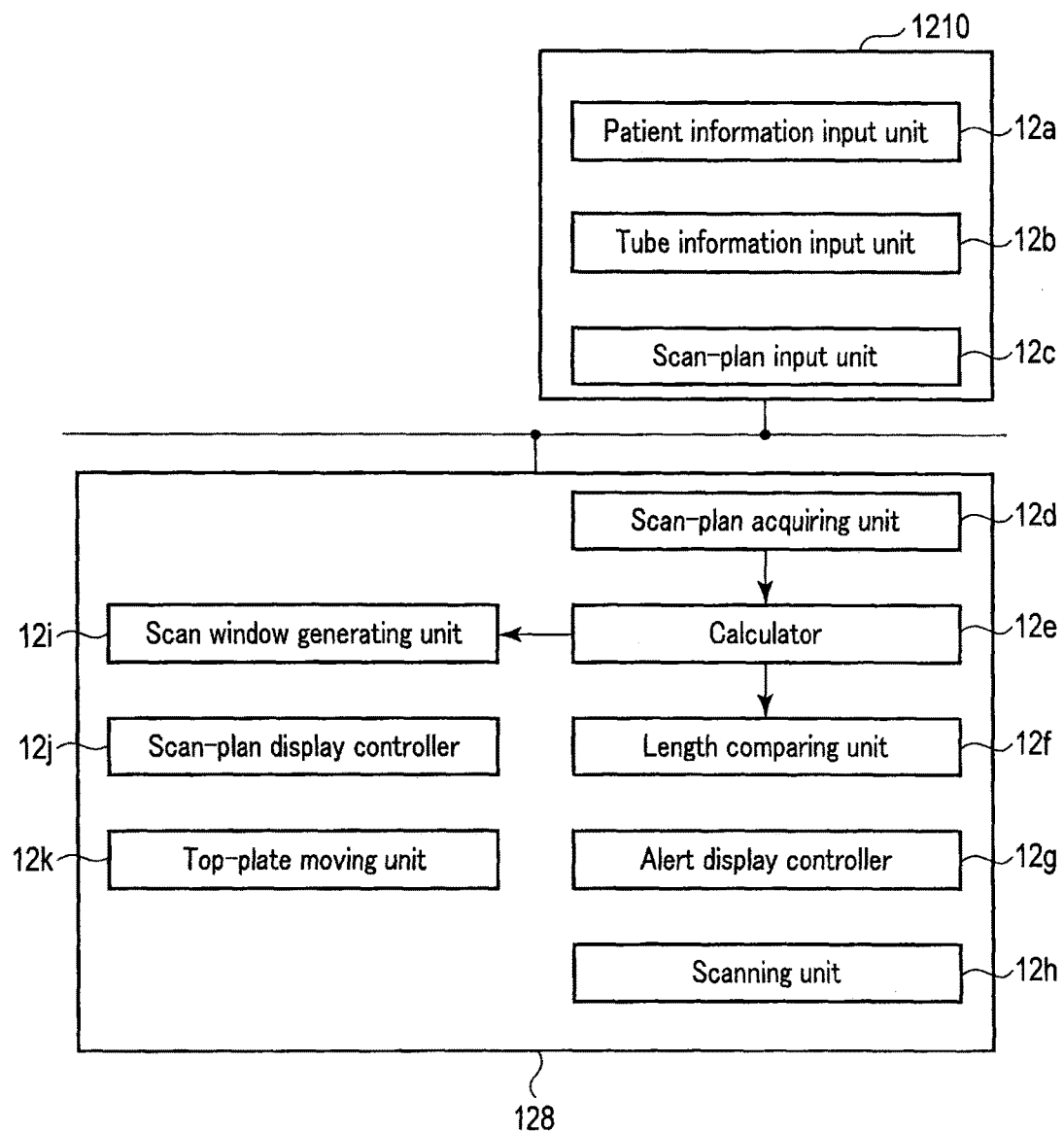
FIG. 2 is a functional block diagram showing an example of the controller 128 and the input unit 1210 shown in FIG. 1.

FIG. 2 is a functional block diagram showing an example of the controller 128 and the input unit 1210 shown in FIG. 1. In FIG. 2, the input unit 1210 includes a patient information input unit 12a, a tube information input unit 12b, and a scan plan input unit 12c as processing functions.

Figure 3:
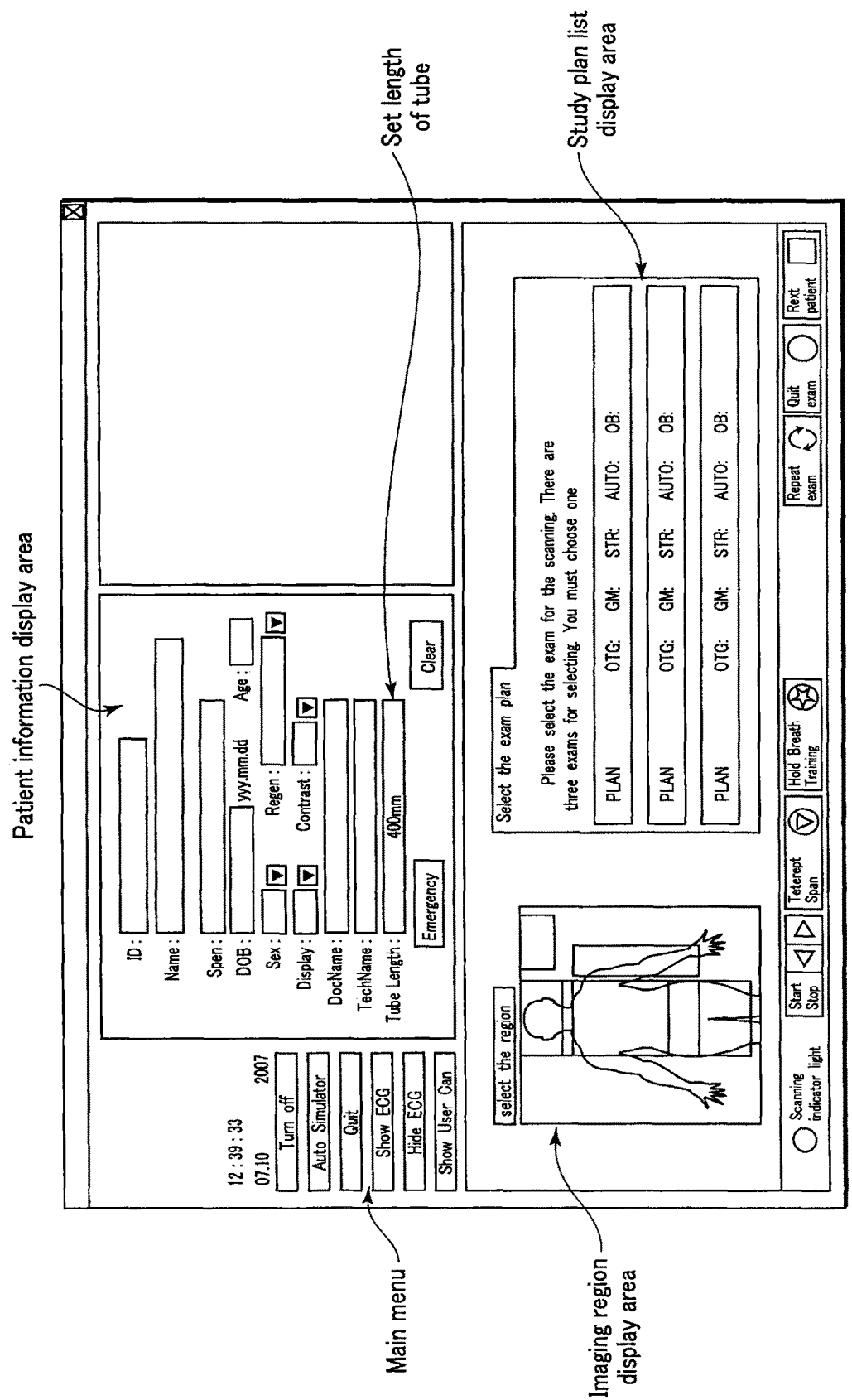
FIG. 3 shows an example of a console screen displayed on a display 129.

The patient information input unit 12a displays a console screen (user interface), for example, as shown in FIG. 3 on the display 129, and realizes a Graphical User Interface (GUI) environment. The patient information input unit 12a prompts an operator to input patient information (individual information such as age, gender and height) of a subject. The input patient information is stored in the storage unit 126.

FIG. 3 shows an example of the console screen. The console screen is displayed on a display (such as the display 129 shown in FIG. 1) different from the gantry mounted display 201. Content based on various information transmitted from the controller 128 to the gantry 11 are displayed on the console screen. For example, information such as a data code of a picture or icon displayed on the gantry mounted display 201, a time when a control signal is generated, a type of the control signal, and an execution result of output of a display item are displayed on the console screen. An operator can confirm display items displayed on the gantry mounted display 201 by viewing the console screen.

The tube information input unit 12b prompts an operator to set a length of a tube. The tube is, for example, an infusion tube or an injection tube for a contrast agent. The length of the tube can be read from descriptions on its package. The length of an electrical cable connected to an electrocardiograph is also important information. Herein, tubes and electrical cables are collectively called "linear members." An operator inputs information including a length of a linear member to the system.

The scan plan input unit 12c prompts the operator to create a scan plan by means of the console screen of FIG. 3. When one or more examination plans are selected, based on a determination of a doctor, from an examination plan list displayed in an examination plan list display area shown in FIG. 3, a scan plan for a patient is automatically created.

Figures 4, 5:
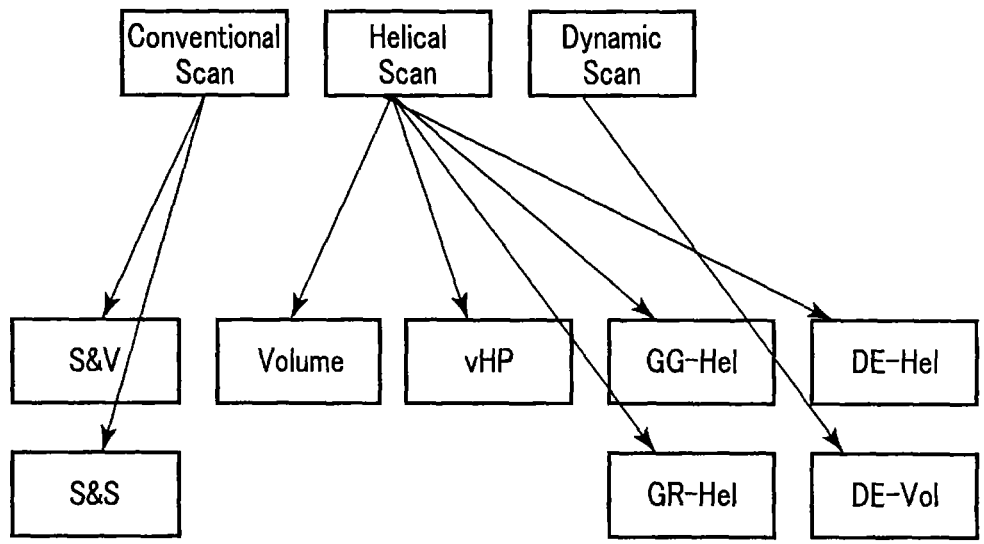
FIG. 4 shows an example of a scan method relating to creation of a scan plan.
FIG. 5 shows a scan mode-scan name relationship.

The scan plan includes a plurality of scan modes, such as a scanogram imaging mode, a helical scan mode, or a dynamic scan mode, which are numbered in serial order. As shown in, for example, FIG. 4, the scan plan can be expressed by information such as a combination and order of scan modes. In FIG. 4, for example, a Conventional Scan is associated with a Scan and View (S & V) and a Scan and Scan (S & S). Appropriate scan methods are selected for each patient. The scan modes abbreviated in FIG. 4 have names shown in FIG. 5.

The scan modes can be selected in any combination in accordance with imaging conditions. However, various combinations of scan modes make it difficult to appropriately determine the moving direction and distance of the top-plate or whether the top-plate moves. Disclosed herein is a technique for eliminating this inconvenience.

The controller 128 includes a scan-plan acquiring unit 12d, a calculator 12e, a length comparing unit 12f, an alert display controller 12g, a scanning unit 12h, a scan window generating unit 12i, a scan-plan display controller 12j, and a top-plate moving unit 12k as processing functions. The scan-plan acquiring unit 12d acquires a scan plan stored in the storage unit 126.

The calculator 12e calculates a moving distance and direction of the top-plate 22 based on the acquired scan plan.

The length comparing unit 12f compares the calculated moving distance of the top-plate 22 with a predetermined tube length (length of the linear member). If the comparison by the length comparing unit 12f shows that the moving distance of the top-plate 22 is longer than the length of the tube, the length comparing unit 12f sends a notice to the alert display controller 12g.

In response to the notice, the alert display controller 12g displays warning information (an alert) on the console screen of the display 129 indicating that the tube is likely to come out. It is also possible to set some margin for a higher level of safety and compare the moving distance with a length obtained by subtracting the margin from the actual length.

The scanning unit 12h scans a subject in accordance with the acquired scan plan. The scan window generating unit 12i generates a scan window for scanning, and displays the scan window on the display 129. Accordingly, a technician can confirm the details of the scan plan and the moving distance etc. of the top-plate 22 on the console screen.

The scan-plan display controller 12j displays on the gantry mounted display 201 at least one of the scan modes based on the acquired scan plan, the moving direction of the top-plate 22, and the moving distance of the top-plate 22. The scan mode and moving direction are displayed in the form of, for example, a picture on the gantry mounted display 201. The moving distance is displayed in, for example, numerals on the gantry mounted display 201.

The top-plate moving unit 12k moves the top-plate 22 in accordance with the scan plan. Next, a plurality of embodiments are described based on the above configuration:

First Embodiment

Figure 6:
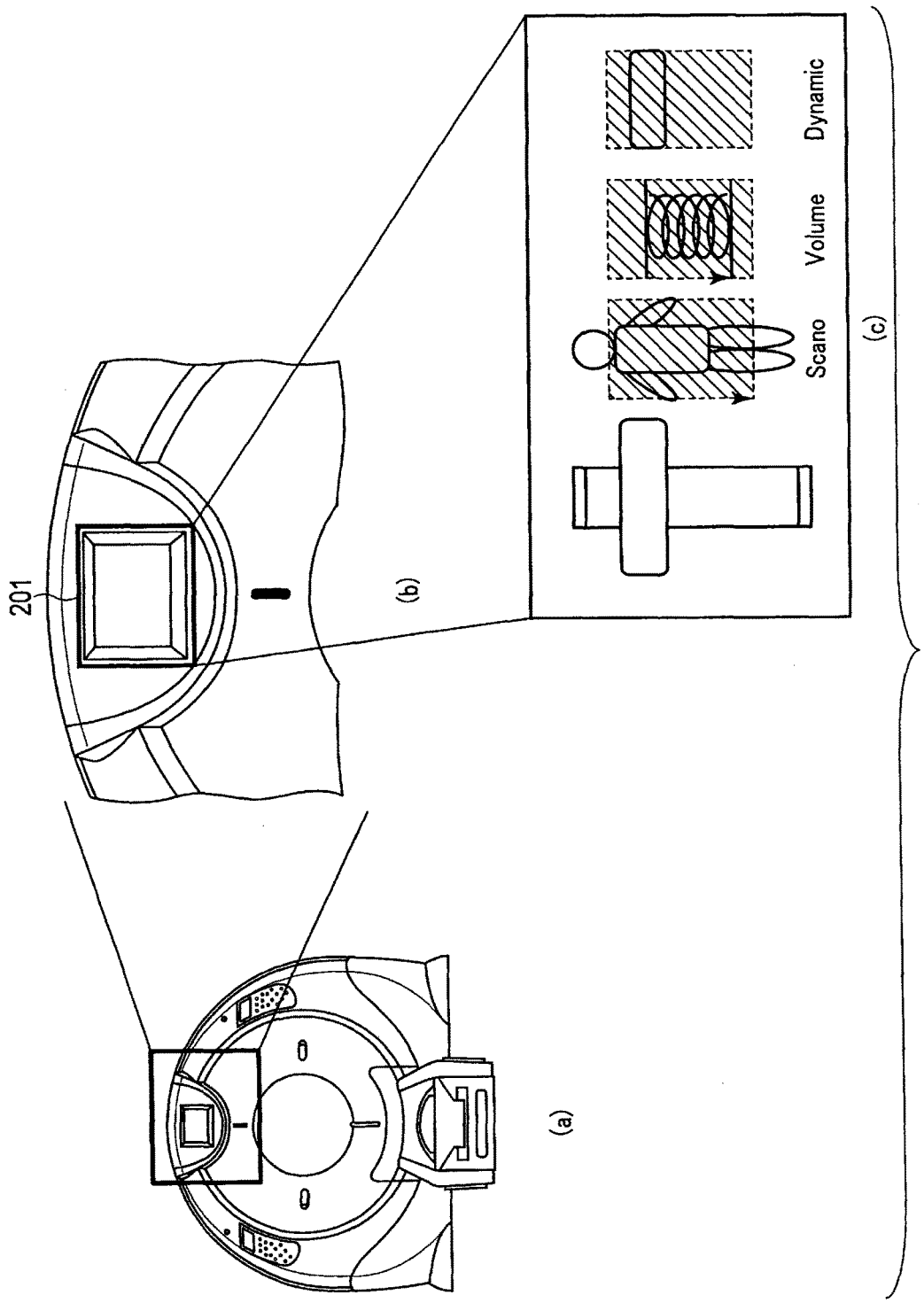
FIG. 6 shows an example of the appearance and displayed content of a gantry mounted display 201.

FIG. 6 shows an example of the appearance and displayed content of the gantry mounted display 201. The gantry mounted display 201 is attached to a panel on the bed 20 side (front panel) of the gantry 11, as shown in, for example, FIGS. 6(a) and (b). For example, as shown in FIG. 6(c), a picture showing the X-ray CT apparatus viewed from above, and icons representing respective scan modes are displayed on the gantry mounted display 201.

Figure 7:
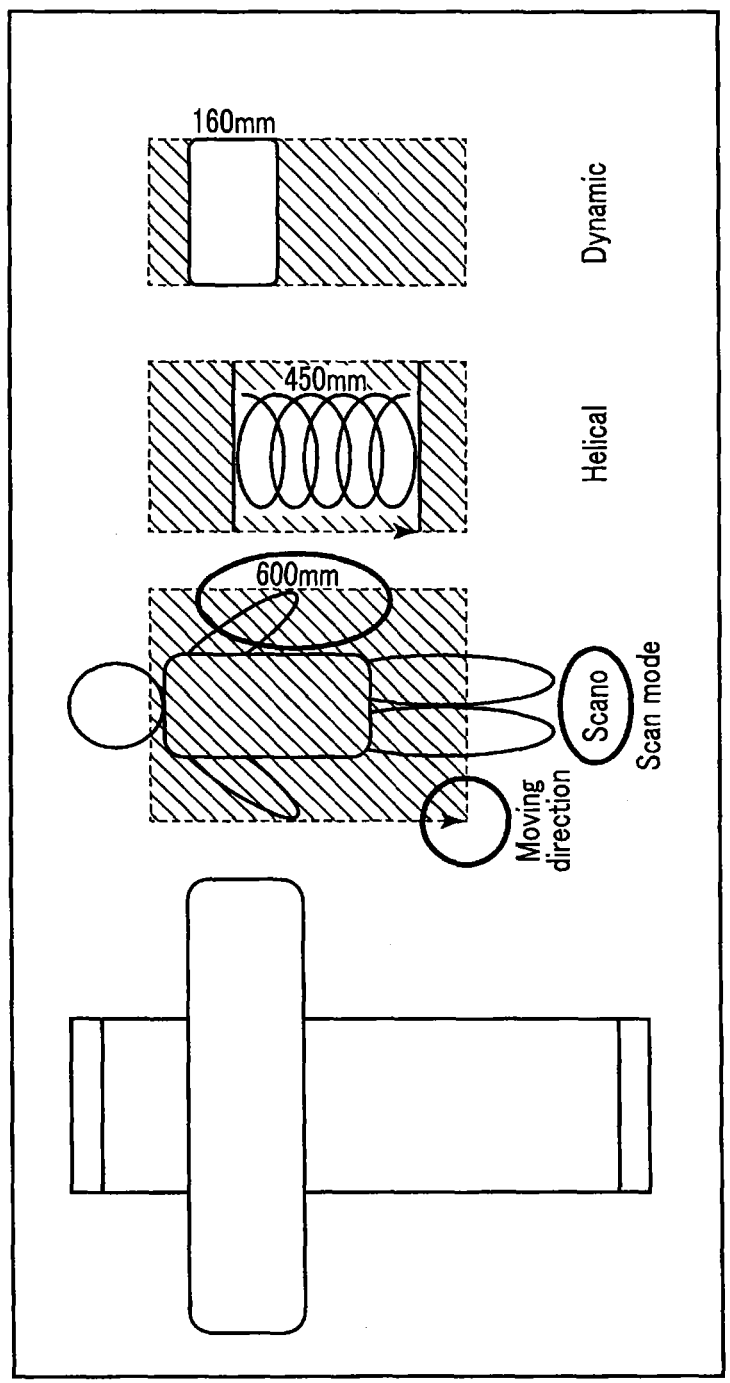
FIG. 7 shows the appearance and displayed content of the gantry mounted display 201 in more detail.

FIG. 7 shows the example of the displayed content of the gantry mounted display 201 in more detail. FIG. 7 shows a scan plan including three scan modes; a scanogram imaging mode (scano mode), a helical imaging mode (helical mode), and a dynamic imaging mode (dynamic mode). In the figure, a scano plan area is indicated by hatching. An actual scan is performed on the scano plan area.

The moving direction of the top-plate 22 is indicated by an arrow. An operator can easily tell IN and OUT directions based on the direction of the arrow. The IN direction is a direction in which a subject moves toward the gantry 11, and the OUT direction is the opposite direction.

A scanogram is acquired by scanogram imaging. The scanogram is an image acquired for considering and setting an imaging range for an actual scan. The scanogram is also called a "scout image."

FIG. 7 shows that the top-plate 22 moves 600 mm in the IN direction in the scano mode, moves 450 mm in the IN direction in the helical mode, and makes no movement in the dynamic mode.

As described above, in the first embodiment, a scan mode for each subject (patient) to be examined, and a moving distance and moving direction of the top-plate 22 are calculated based on a scan plan. The calculated information is symbolically displayed on the gantry mounted display 201 attached to the gantry 11. Accordingly, an operator can easily tell the actual moving distance of the top-plate 22 by viewing the gantry mounted display 201.

Since a scan plan of a subject patient can be recognized at a glance, a technician or a nurse in an examination room need not confirm a scan plan with an operator in a console room for every examination. Namely, a technician can recognize the scan mode and the top-plate moving distance and direction without leaving an examination room to confirm them with an operator. This configuration greatly contributes to adjusting a position of a patient in accordance with a scan plan, and can eliminate inconvenience to the user and significantly reduce the examination time.

In existing techniques, a user goes to a scan console in a console room separate from an examination room, confirms a scan plan, and recognizes an approximate moving distance of the top-plate. Then, the moving distance is estimated depending on the part to be imaged, and a contrast agent and a drip are set in the examination room in an area determined in consideration of the moving distance and a margin.

However, due to various scan modes recently available, it has been difficult to determine, for example, whether the top-plate gradually moves (as in helical imaging) or moves at once (as in multi-row imaging). Furthermore, it has been difficult to make sure whether the moving distance of the top-plate does not cause any problem for the patient.

According to the first embodiment, a moving direction and moving distance (including whether the top-plate moves or not) of the top-plate and a scan mode according to a scan plan are displayed on a monitor of a gantry in an easily-viewable manner. Accordingly, a technician and a nurse in an examination room can easily know the movement of the top-plate. Thus, peripheral devices (peripheral objects) including medical appliances can be set at the most appropriate positions to minimize danger.

Consequently, danger caused by movement of the top-plate can be predicted, and appropriate measures can be taken in advance.

Second Embodiment

Figure 8:
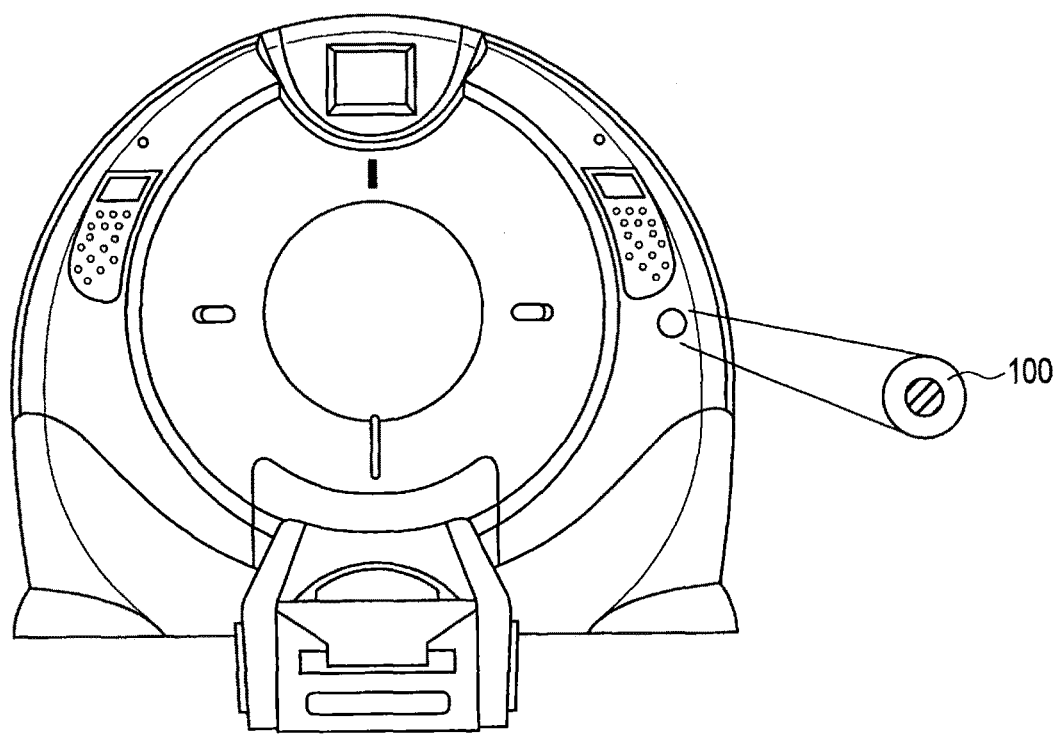
FIG. 8 is an appearance diagram showing an example of a medical image diagnosis system 10 according to the second embodiment, which is viewed from the front panel side.

FIG. 8 is an appearance diagram showing an example of the medical image diagnosis system 10 according to the second embodiment, which is viewed from the front panel side. A simulate button 100 is provided on the front panel of the gantry 11, preferably at an easy-to-operate position.

When a user operates the simulate button 100, the top-plate moving unit 12k (FIG. 2) of the controller 128 moves the top-plate 22 in a non-radiating simulation, based on the moving distance and moving direction calculated by the calculator 12e. Namely, when the simulate button 100 is operated, the top-plate 22 makes a movement corresponding to the scan plan. At this time, the high voltage generator 121 is turned off, and the X-ray tube 13 is inactivated. Accordingly, movement of the top-plate 22 at the time of actual imaging can be simulated without radiation occurring.

Figure 9:
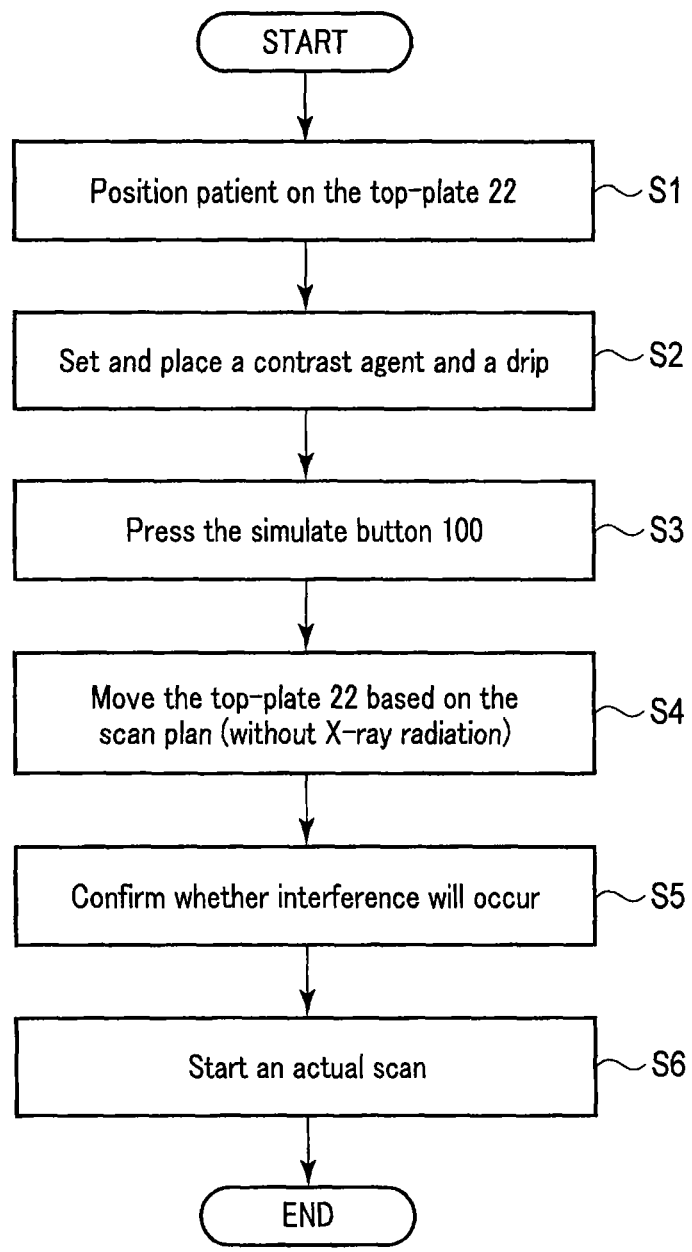
FIG. 9 is a flowchart showing an example of a procedure at the medical image diagnosis system 10 according to the second embodiment.

FIG. 9 is a flowchart showing an example of a procedure at the medical image diagnosis system 10 according to the second embodiment. First, a patient lies upon the top-plate 22 (step S1), and is connected to tubes after a contrast agent and a drip are arranged in an examination room (step S2).

When the preparation is completed, a technician in the examination room presses the simulate button 100 (step S3). The controller 128 moves the top-plate 22 in accordance with the scan plan as will be done in an actual scan. For example, if the scan plan includes the helical imaging mode, the top-plate 22 slowly moves in the Z-direction in that mode. If the scan plan includes the multi-row imaging mode, the top-plate 22 moves discontinuously in a stepwise manner. Accordingly, when the simulate button 100 is pressed, the movement of the top-plate 22 to be made in an actual scan is simulated. Consequently, not only the movement of a subject, but also tension and changes in sagging of a linear member can be simulated in advance.

In this stage, the X-ray tube is kept off. Therefore, X-rays are not radiated (step S4). Accordingly, the unnecessary exposure of the subject to radiation can be prevented during top-plate movement simulation.

A technician carefully watches the patient and tube moving together with the top-plate 22, and confirms that the tube does not interfere, i.e., come into contact, with the bed 20 or the gantry 11, and that the tube is not pulled out (step S5). If there is no problem in the procedure up to this point, an actual scan is started (step S6), and imaging with X-ray radiation of a dose corresponding to the scan plan is started.

As described above, in the second embodiment, the simulate button 100 provided on the gantry 11 enables movement of the top-plate 20 without radiation occurring. This embodiment may be combined with the first embodiment. After viewing scan information displayed on the gantry mounted display 201, a technician rearranges the contrast agent and the drip. Next, the technician sets a patient's position, and then presses the simulate button 100 to only move the top-plate 22 without radiating X-rays. This makes it possible to confirm if there is interference with peripheral equipment (peripheral objects), tubes, or the like.

As an actual operation, the following operation may be performed: the top-plate 22 starts to move when the simulate button 100 is pressed, and keeps moving while the simulate button 100 continues to be pressed, and stops when a hand releases the button, and returns to the home position when the simulate button 100 is pressed again. Namely, pressing the button corresponds to moving the top-plate, releasing the button corresponds to stopping the top-plate, and pressing the button again corresponds to returning the top-plate to the home position.

To realize such an embodiment, the top-plate moving unit 12k starts moving the top-plate 22 when the simulate button 100 is pressed, and moves the top-plate 22 while the simulate button 100 is being pressed. The top-plate moving unit 12k stops the top-plate 22 when the simulate button 100 is released, and then returns the top-plate 22 to the home position when the simulate button 100 is pressed again.

Alternatively, the top-plate 22 may be moved in response to the first pressing and releasing of the simulate button 100; stopped in response to the second pressing and releasing; and returned to the home position in response to the third pressing and releasing.

Consequently, as in the first embodiment, danger caused by movement of the top-plate can be predicted, and appropriate measures can be taken in advance in the second embodiment.

Third Embodiment

Figure 10:
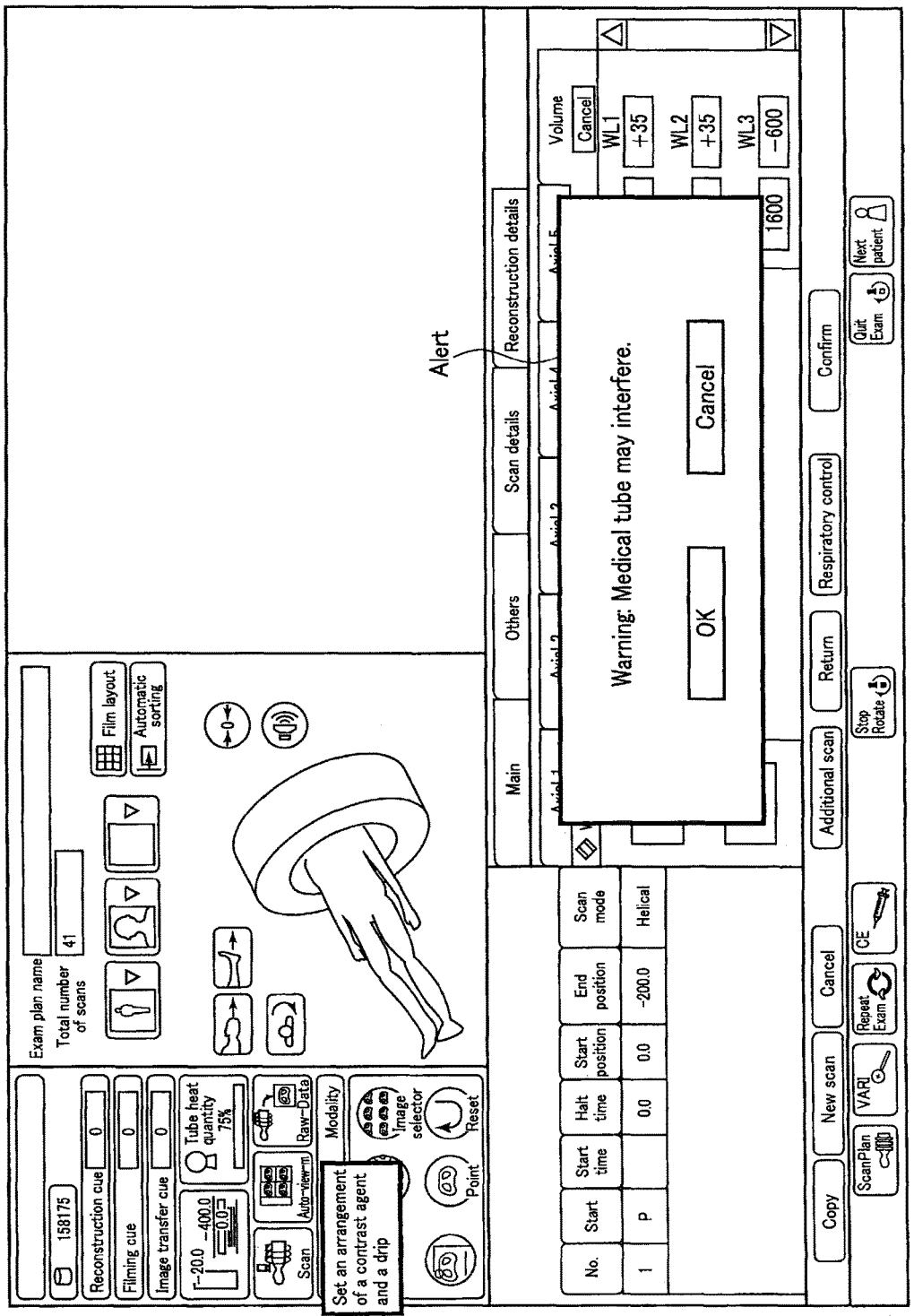
FIG. 10 is a diagram showing an example of an alert displayed on the console screen.

FIG. 10 shows an example of the console screen displayed on the display 129 according to the third embodiment. The alert shown in FIG. 10 is displayed on the console screen when a scan plan (examination plan) is selected, for example. The installation position of the injector and the length of the tube are input in advance by means of the console screen. When a scan plan is selected, the moving distance and moving direction of the top-plate 22 are calculated. As a result of the calculation, if the moving distance of the top-plate 22 is excessively longer than the length of the tube, an alert indicating that the tube may come out or interfere is displayed.

Figure 11:
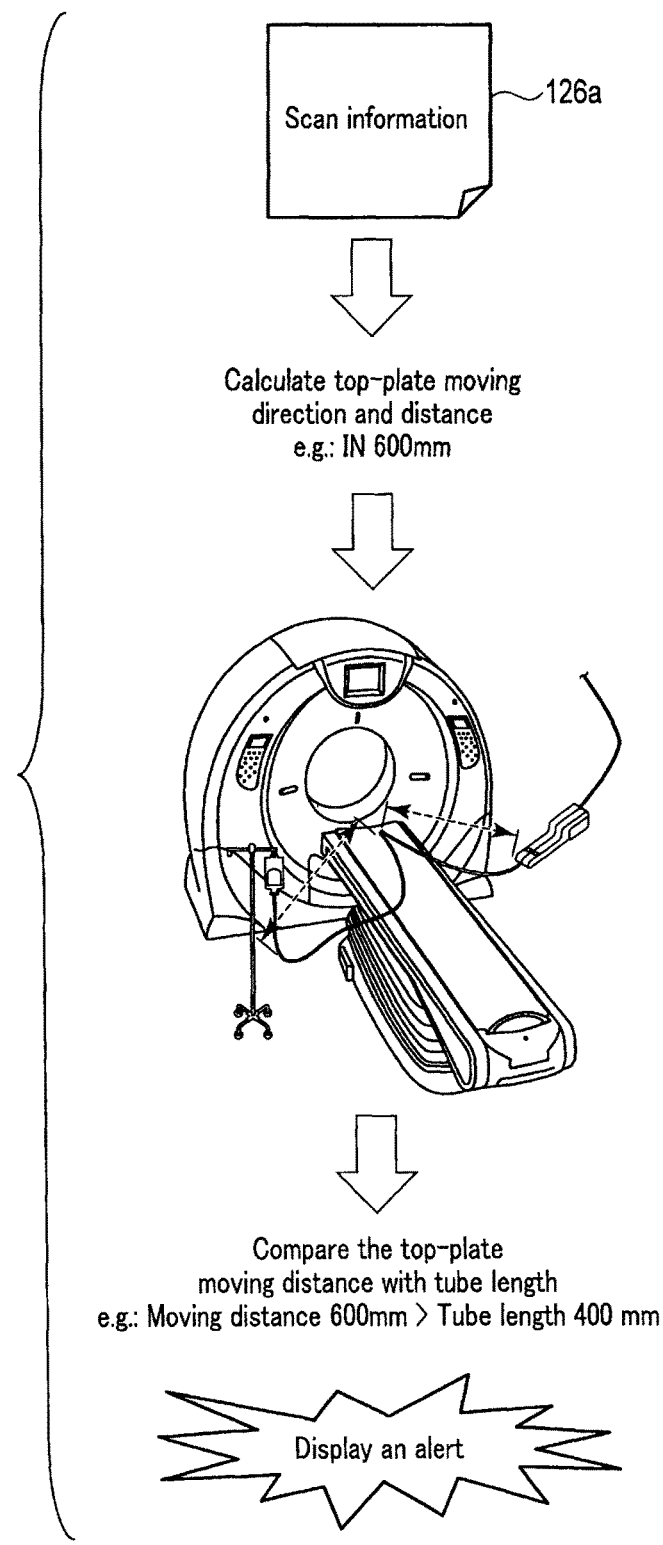
FIG. 11 is a schematic diagram illustrating an example of a procedure in a third embodiment.

As shown in FIG. 11, the moving direction and moving distance of the top-plate 22 are calculated based on scan information 126a stored in advance. Let us assume that the calculation result is 600 mm in the IN direction, for example. This distance is longer than the tube length of 400 mm. Thus, the tube may be pulled and come out as the subject moves toward the gantry 11 together with the top-plate 22. In such a case, an alert is displayed on the console screen in the third embodiment.

As described above, in the third embodiment, the length of the contrast agent tube and arrangement of medical appliances in the examination room are set in advance when patient information or examination information is input. Based on the information, the tube length is compared with the top-plate moving distance when a scan plan is selected, and an alert message is displayed on the screen when the tube length is shorter than the top-plate moving distance.

This configuration enables more accurately determining, before scanning, if a tube will or will not come out. Consequently, as in the first and second embodiments, danger caused by movement of the top-plate can be predicted, and appropriate measures can be taken in advance in the third embodiment.

According to the first to third embodiments, a patient can be protected by preventing a medical tube from coming out due to top-plate movement, and unnecessary radiation caused by re-imaging can be prevented.

Based on the technique disclosed in the first to third embodiments, for example, the following procedures can be taken in clinical sites:

(1) Display on the console screen a list of some scan plans in accordance with the examination purpose and patient information (adult/child).

(2) Input from the console screen the length of a tube of an injector or drip, and arrangement of the injector or drip.

(3) Select an examination plan determined to be appropriate by a doctor from information displayed on the console screen, and create a scan plan.

(4) Display an alert message on the screen when the length of the tube of the injector or drip (or a length obtained by subtracting a margin from the actual length) is shorter than the moving distance.

(5) Correct a scan range and a scan position.

(6) Display the scan plan on the gantry mounted display 201.

(7) If necessary, simulate top-plate movement by operating the simulate button 100.

(8) Perform scanogram imaging.

(9) Make a minor correction of the scan range and the scan position based on the scanogram.

(10) Display a corrected scan plan on the gantry mounted display 201.

(11) If necessary, simulate top-plate movement by operating the simulate button 100.

(12) If safety is confirmed by the above procedure, perform an actual scan.

The embodiments are not limited to the ones above-described.

For example, in the above-described embodiments, the length of the tube main body is compared with the moving distance of the top-plate 22. Alternatively, the length of sagging of the tube may be compared with the moving distance of the top-plate 22 to determine if the tube may come out.

The entrance region or deceleration region of the top-plate 22 may be indicated by, for example, colors, on the scanogram imaging region (scano region) or helical region displayed on the gantry mounted display 201. This gives a hint about a margin for preventing the tube from coming out.

The simulation of top-plate movement under radiation may be instructed by not only the simulate button 100, but also by a mouse-clicking operation in the console room. When top-plate movement is simulated, instead of all of the processes, only the process in which the moving distance becomes maximum (such as scano), or a scan process may be simulated. In this case, a reduced examination process, i.e., top-plate movement corresponding to a scan mode in which the moving distance of the top-plate becomes maximum in the scan plan is simulated. The moving speed of the top-plate does not need to be the same in simulation and in imaging. It may be lower or higher than the speed at the time of imaging (actual scan).

In the third embodiment, an alert message is displayed. Instead of the alert message, however, a sound, a voice, or flashing of a warning lamp may be used for warning.

The patient information and examination information (including information on a contrast agent tube) may be manually input by an operator, or may be acquired from another system (such as an electronic health record system or a radiation therapy management system) via a network.

The functions explained in the above embodiment can be implemented by one or a plurality of processing units. The processing units can be, for example, dedicated or general-purpose processor, circuit (circuitry), processing circuit (circuitry), operation circuit (circuitry), arithmetic circuit (circuitry), or Application Specific Integrated Circuit (ASIC), Simple Programmable Logic Device (SPLD), Complex Programmable Logic Device (CPLD), and Field Programmable Gate Array (FPGA).

Each processing unit may be implemented as a processor including an electronic circuit such as a memory. The processing unit can include a processor that functions by a program stored in a memory. The processing unit can include an application specific integrated circuit (IC) or a conventional circuit element to execute the above-described functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image diagnosis apparatus capable of imaging a subject based on a scan plan, the medical image diagnosis apparatus comprising:
a gantry which images the subject;
a bed including a top-plate on which the subject is mounted;
a first display on a console;
a second display attached to the gantry; and
a controller which controls the second display to display, based on the scan plan, at least one of a moving distance of the top-plate, a moving direction of the top-plate, and a scan mode based on the scan plan on at least the second display.

2. The medical image diagnosis apparatus of claim 1, wherein
the controller controls the second display to display at least one of the moving direction and the scan mode on the second display in a form of a picture.

3. The medical image diagnosis apparatus of claim 1, wherein
the controller controls the second display to display the moving distance on the second display in numerals.

4. The medical image diagnosis apparatus of claim 1, wherein
the controller outputs a warning when the moving distance is longer than a length of a linear member extending from a medical appliance and attached to the subject.

5. The medical image diagnosis apparatus of claim 4, further comprising:
an input unit for setting the length of the linear member.

6. A medical image diagnosis apparatus capable of imaging a subject by radiating a radial ray to the subject based on a scan plan, the medical image diagnosis apparatus comprising:
a gantry which images the subject;
a bed including a top-plate on which the subject is positioned; and
circuitry configured to
calculate a moving distance and a moving direction of the top-plate based on the scan plan; and
execute a test movement for actually moving the top-plate without radiating based on the calculated moving distance and moving direction.

7. The medical image diagnosis apparatus of claim 6, wherein
the gantry includes an operation button, and
the circuitry is configured to move the top-plate based on an operation of the operation button.

8. The medical image diagnosis apparatus of claim 7, wherein
the circuitry is configured to start moving the top-plate when the operation button is pressed, move the top-plate while the operation button continues to be pressed, and stop the top-plate when the operation button is released.

9. The medical image diagnosis apparatus of claim 6, wherein
the circuitry is configured to simulate movement of the top-plate corresponding to a scan mode in which the moving distance of the top-plate becomes maximum in the scan plan.

* * * * *